United States Patent [19]

Hammerschmidt et al.

[11] 4,427,601
[45] Jan. 24, 1984

[54] PROCESS FOR PREPARING 1-AMINO-2-NAPHTHOL-4-SULPHONIC ACID (AMIDOL ACID)

[75] Inventors: Erich Hammerschmidt, Bergisch-Gladbach; Horst Behre, Odenthal; Heinz U. Blank, Odenthal; Otto Lindner, Bergisch-Gladbach, all of Fed. Rep. of Germany

[73] Assignee: Bayer Aktiengesellschaft, Leverkusen, Fed. Rep. of Germany

[21] Appl. No.: 439,474

[22] Filed: Nov. 5, 1982

[30] Foreign Application Priority Data

Nov. 27, 1981 [DE] Fed. Rep. of Germany ....... 3147152

[51] Int. Cl.³ .......................................... C07C 143/66
[52] U.S. Cl. .................................................. 260/509

[58] Field of Search ........................................ 260/509

[56] References Cited
PUBLICATIONS

N. Donaldson, "The Chemistry and Technology of Naphthalene Compounds", Edward Arnold (Publishers) Ltd., London, 1958, pp. 325–326.

*Primary Examiner*—Nicky Chan
*Attorney, Agent, or Firm*—Sprung, Horn, Kramer & Woods

[57] ABSTRACT

The process for preparing 1-amino-2-naphthol-4-sulphonic acid by acidifying 3-oxo-4-hydroxyimino-1,2,3,4-tetrahydronaphthalene-1-sulphonic acid or its alkali metal salt in the presence of hydrogen sulphite is carried out in the presence of iron ions.

10 Claims, No Drawings

PROCESS FOR PREPARING 1-AMINO-2-NAPHTHOL-4-SULPHONIC ACID (AMIDOL ACID)

The present invention relates to a process for preparing 1-amino-2-naphthol-4-sulphonic acid (amidol acid) by reacting 3-oxo-4-hydroxyimino-1,2,3,4-tetrahydronaphthalene-1-sulphonic acid with hydrogen sulphite (bisulphite) and a mineral acid.

Amidol acid is an important intermediate product in the preparation of dyestuffs (Ullmanns Enzyklopädie der technischen Chemie (Ullmann's Encyclopaedia of Industrial Chemistry), 4th edition, volume 17, page 100).

Its preparation has been described, for example, in BIOS Final Report No. 986/I, No. 22, page 44–45 (compare also Ullmann, loc. cit.) and in Organic Synthesis, Col. vol. II, page 42 (1943), and involves reacting nitrosated β-naphthol with sodium hydrogen sulphite and subsequent acidification with sulphuric acid. The aqueous solutions of 3-oxo-4-hydroxyimino-1,2,3,4-tetrahydronaphthalene-1-sulphonic acid, which are obtained here as intermediate products, can also be obtained by bisulphite addition to 1,2-naphthoquinone-1-oxime (1-nitroso-2-naphthol) and then acidified in the presence of at least equimolar amounts of bisulphite and heated (Liebigs Ann. 638, 76 (1960)). The instructions for preparing amidol acid indicated in the BIOS Final Report mentioned have considerable disadvantages due to the time before complete reaction of 36 to 40 hours and the resulting low space/time yields. The yield data given in Organic Synthesis refer to dry yields, the amidol acid contents of which are not mentioned. The yields of 100% pure amidol acid are therefore below those indicated.

A process has now been found for preparing 1-amino-2-naphthol-4-sulphonic acid (amidol acid) by acidifying 3-oxo-4-hydroxyimino-1,2,3,4-tetrahydronaphthalene-1-sulphonic acid or its alkali metal salt in the presence of hydrogen sulphite, which is characterised in that the reaction is carried out in the presence of iron ions.

3-Oxo-4-hydroxyimino-1,2,3,4-tetrahydronaphthalene-1-sulphonic acid (hydrogen sulphite addition compound) can be obtained, according to the state of the art, for example by nitrosation of β-naphthol and the subsequent addition of an alkali metal hydrogen sulphite. This reaction produces this addition compound in the form of its alkali metal salt, for example the sodium salt or potassium salt, by salting out, for example with sodium chloride, or the free acid by subsequent acid treatment of such an alkali metal salt. According to the invention, it is possible to use not only the acid but also its alkalli metal salts. Furthermore, it is possible to use not only an aqueous solution of the previously isolated 3-oxo-4-hydroxyimino-1,2,3,4-tetrahydronaphthalene-1-sulphonic acid or its alkali metal salt, but also aqueous reaction mixtures formed by reaction of nitrosated β-naphthol with hydrogen sulphite.

According to the invention, the preparation of amidol acid is carried out in the presence of iron ions. The iron ions can be added to the reaction mixture in the form of iron compounds from which iron ions can be formed in the reaction mixture. Examples which may be mentioned of such compounds are salts, hydroxides, soluble oxides and complex compounds of iron. Examples which may be mentioned of salts are sulphates, nitrates, chlorides, bromides, iodides, carbonates, formates, acetates and phosphates. Examples which may be mentioned of hydroxides and soluble oxides are $Fe(OH)_2$, $Fe(OH)_3$, $FeO$ and $Fe_2O_3$. The iron compounds mentioned can be used not only singly but also as a mixture of several of these compounds. Moreover, the iron compounds mentioned can be added in solid form or as a solution in water or in non-oxidising acids.

Trivalent or divalent iron ions or a mixture of trivalent and divalent iron ions may also be mentioned as iron ions for the process according to the invention. Divalent iron ions or a mixture which predominantly contains divalent iron ions are preferable according to the invention. Such mixtures are present in many industrially available salts of divalent iron which, due to their contact with atmospheric oxygen, contain a low proportion of salt of trivalent iron.

Iron is used in an amount of 0.02 mol to 3 mols of iron ions per mol of hydrogen sulphite addition compound, preferably 0.05 to 2 mols, particularly preferably 0.1 to 1 mol of iron ions being used. Larger amounts of iron are not harmful but without particular benefit.

The process according to the invention is carried out with acidification of the reaction batch. This acidification down to pH values of about 1.5 to minus 0.5 can be effected by any non-oxidising acids. Examples which may be mentioned are sulphuric acid, phosphoric acid and hydrogen halide acids, preferably sulphuric acid.

In a preferable variant, an iron-containing waste dilute acid, as obtained, for example, in the preparation of titanium dioxide, is used. Such a waste sulphuric acid simultaneously contains the iron ions necessary according to the invention and the sulphuric acid required for the acidification. Typical waste sulphuric acids from the preparation of titanium dioxide contain about 20 to 25% by weight of $H_2SO_4$ and about 10 to 13% by weight of $FeSO_4$.

The reaction mixture also contains at least 1 mol of additional hydrogen sulphite per mol of hydrogen sulphite addition compound. By heating the reaction mixture to which hydrogen sulphite and the acid have been added to 10° to 120° C., preferably 30° to 80° C., the formation of amidol acid, which already commences during the acidification, is completed.

Compared to processes without the use of iron ions, considerable increases in yield are obtained according to the invention. The use of iron ions is also economical owing to the considerable increase of the space/time yield compared to the state of the art and at the same time ecologically acceptable. In the special process variant where waste dilute acid from the preparation of titanium dioxide is used, in addition inexpensive sulphuric acid is available which already contains the necessary amount of ferrous sulphate and which at the same time is used for a sensible purpose.

EXAMPLE 1

1 mol of isolated and recrystallised bisulphite addition compound (3-oxo-4-hydroxyimino-1,2,3,4-tetrahydronaphthalene-1-sulphonic acid) in the form of its sodium salt is dissolved in 2,500 ml of water, and 1.5 mols of sodium bisulphite as a 38% strength by weight aqueous solution and 0.8 mol of iron(II) sulphate are added to the solution. The dark reaction solution is adjusted with 50% strength sulphuric acid at 25° C. to pH 0.5 and the formation of amidol acid slowly commences. The reaction is completed by heating for 5 hours at 50° C. Subsequently the suspension is cooled down to 20° C. and the precipitated amidol acid is filtered off and washed. 90% of the theoretical yield, relative to the bisulphite addition compound, is obtained.

EXAMPLE 2

0.6 mol of iron(II) sulphate is added to 2,900 ml of an aqueous solution of the bisulphite addition compound, prepared by nitrosation of 1 mol of β-naphthol and addition of bisulphite by adding 2.5 mols of sodium bisulphite as a 38% by weight strength aqueous solution (see BIOS Final Report loc.cit.) and the mixture is then acidified with 600 ml of 70% strength sulphuric acid. Amidol acid starts to precipitate already during the acidification. The reaction is completed by heating for 5 hours at 50° C. After cooling down to 20° C., isolating and washing the product, 86% of the theoretical yield of amidol acid, relative to β-naphthol, is obtained.

EXAMPLE 3

A solution, prepared as in Example 2, of the bisulphite addition compound is acidified with 2,500 g of waste dilute acid from the preparation of titanium dioxide (22-23% by weight of $H_2SO_4$ and 11-11.5% by weight of $FeSO_4$). The further procedure corresponds to Example 2. 86.5% of the theoretical yield, relative to β-naphthol, is obtained.

EXAMPLE 4

(Comparative experiment according to BIOS Final Report No. 986/I, Item No. 22, page 44-45; compare also Ullmann, 4th edition, volume 17, pages 100 and 125)

1 mol of β-naphthol is nitrosated according to the instructions and then reacted with bisulphite. 125 g of sodium chloride are added to the resulting solution of the bisulphite addition compound which still contains small amounts of black flakes, and after the sodium chloride has dissolved, the solution is poured onto 1,250 ml of 5.5% strength sulphuric acid. By further adding 175 g of 78% strength $H_2SO_4$, the reaction mixture is still more strongly acidified and then externally heated to 40° C. Initially the temperature in fact increases to about 50° C. and then slowly decreases. During this step, amidol acid precipitates as a pale grey product. To complete the crystallisation, the mixture is allowed to stand for a further 40 hours, occasionally interrupted by stirring. After isolating and washing the product, 79% of the theoretical yield, relative to β-naphthol, is obtained.

EXAMPLE 5

(Comparative experiment according to Organic Synthesis Coll. vol. I, page 411 (1941) and Coll. vol. II, page 42 (1943))

2.1 mols of β-naphthol are nitrosated according to the instructions, isolated and reacted to give the bisulphite addition product. After removal of the dark flakes by clarification, a yellow-brown clear solution is obtained which is diluted to 7 liters. While stirring the solution vigorously, it is acidified with 400 ml of concentrated sulphuric acid. This increases the temperature of the reaction mixture to 50° C. in the course of 2 hours. After a further 3 hours, the product is isolated and washed. 75% of the theoretical yield, relative to β-naphthol, of 100% pure amidol acid is obtained.

EXAMPLE 6

Materials and procedure in each case analogous to Examples 1 and 2, but without the addition of the iron salt.

| Comparative experiment to | Yield |
|---|---|
| Example 1 | 81%, relative to bi-sulphite addition compound |
| Example 2 | 79%, relative to β-naphthol |

What is claimed is:

1. In a process for preparing 1-amino-2-naphthol-4-sulphonic acid by acidifying 3-oxo-4-hydroxyimino-1,2,3,4-tetrahydronaphthalene-1-sulphonic acid or its alkali metal salt in the presence of hydrogen sulphite, the improvement which comprises carrying out the process in the presence of iron ions.

2. A process according to claim 1, wherein the reaction is carried out in the presence of 2-valent iron ions.

3. A process according to claim 1, wherein at least 0.02 mol of iron ions is employed per mol of 3-oxo-4-hydroxyimino-1,2,3,4-tetrahydronaphthalene-1-sulphonic acid.

4. A process according to claim 1, wherein 0.02 to 3 mols of iron ion are employed per mol of 3-oxo-4-hydroxyimino-1,2,3,4-tetrahydronaphthalene-1-sulphonic acid.

5. A process according to claim 1, wherein 0.05 to 2 mols of iron ions are employed per mol of 3-oxo-4-hydroxyimino-1,2,3,4-tetrahydronaphthalene-1-sulphonic acid.

6. A process according to claim 1, wherein 0.1 to 1 mol of iron ions is employed per mol of 3-oxo-4-hydroxyimino-1,2,3,4-tetrahydronaphthalene-1-sulphonic acid.

7. A process according to claim 1, wherein the iron ions are added in the form of an iron salt, iron hydroxide, soluble iron oxide or iron complex.

8. A process according to claim 1, wherein the iron ions are added in the form of a sulphate, nitrate, chloride, bromide, iodide, carbonate, formate, acetate or phosphate of iron.

9. A process according to claim 1, wherein the iron ions are added in the form of a hydroxide or soluble oxide of iron.

10. A process according to claim 1, wherein the iron ions are added in the form of an iron-containing waste sulphuric acid.

* * * * *